United States Patent
Schmidlin et al.

(10) Patent No.: US 11,103,420 B2
(45) Date of Patent: Aug. 31, 2021

(54) MEDICAL DEVICE, PROGRAMMING DEVICE, WIRELESS TERMINAL, AND MEDICAL SYSTEM

(71) Applicant: Novartis AG, Basel (CH)

(72) Inventors: Alain Schmidlin, Basel (CH); Mario Iobbi, Basel (CH); Erich Studer, Basel (CH); Andrew Bryant, Basel (CH); Chinmay Deodhar, Pune (IN); Rajan Patel, Menlo Park, CA (US); Samuel Coendet, Munich (DE); Vivek Gajera, Pune (IN); Prakash Parmar, Pune (IN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/494,069

(22) PCT Filed: Feb. 5, 2018

(86) PCT No.: PCT/EP2018/052802
§ 371 (c)(1),
(2) Date: Sep. 13, 2019

(87) PCT Pub. No.: WO2018/166712
PCT Pub. Date: Sep. 20, 2018

(65) Prior Publication Data
US 2020/0107992 A1    Apr. 9, 2020

Related U.S. Application Data

(60) Provisional application No. 62/471,377, filed on Mar. 15, 2017.

(30) Foreign Application Priority Data

Mar. 31, 2017 (EP) .................................... 17164156

(51) Int. Cl.
*G16H 20/13* (2018.01)
*G16H 20/17* (2018.01)
(Continued)

(52) U.S. Cl.
CPC ............ *A61J 1/14* (2013.01); *G06K 7/10356* (2013.01); *G06K 19/07773* (2013.01);
(Continued)

(58) Field of Classification Search
CPC ........ G16H 20/13; G16H 20/17; G16H 40/63; H04W 76/14; H04B 5/0031; A61M 5/142;
(Continued)

(56) References Cited

U.S. PATENT DOCUMENTS 3,583,399 A    6/1971  Ritsky
5,957,889 A    9/1999  Poulsen et al.
(Continued)

FOREIGN PATENT DOCUMENTS

EP    1755704 A1    2/2007
EP    2249275 A1    11/2010
(Continued)

OTHER PUBLICATIONS

"Using RFID to Track Critical Medical Device Information: Vizinex." Vizinex RFID, Jul. 7, 2015, (6 pages), https://web.archive.org/web/20150711212300/https://www.vizinexrfid.com/using-rfid-track-critical-medical-device-information/.
(Continued)

*Primary Examiner* — Pablo N Tran
(74) *Attorney, Agent, or Firm* — Moore & Van Allen PLLC; Henry B. Ward, III

(57) ABSTRACT

A medical device (100) comprises a container receiver unit (110) configured to receive and hold a container (120), wherein the container (120) accommodates a pharmaceuti-
(Continued)

cal product (125) and comprises a first communication tag (130) configured to store information regarding the pharmaceutical product (125), a reader unit (140) configured to wirelessly read the information from the first communication tag (130), and a control unit (150) configured to control the medical device (100) based on the information read from the first communication tag (130). The medical device (100) further comprises an opening or a transparent window (165) allowing to at least partially see from the outside the container (120) inserted into the container receiver unit (110), wherein the reader unit (140) comprises a first antenna unit (142, 144), and the container (120) inserted into the container receiver unit (110) is located between (i) the opening or the transparent window (165) and (ii) the first antenna unit (142, 144).

14 Claims, 7 Drawing Sheets

(51) Int. Cl.
*A61J 1/14* (2006.01)
*G16H 40/40* (2018.01)
*G16H 40/63* (2018.01)
*G06K 7/10* (2006.01)
*G06K 19/077* (2006.01)

(52) U.S. Cl.
CPC ............. *G16H 20/13* (2018.01); *G16H 40/40* (2018.01); *G16H 40/63* (2018.01); *A61J 2205/60* (2013.01)

(58) Field of Classification Search
CPC ......... A61M 39/10; A61M 5/14; G06F 19/00; G06K 19/077
See application file for complete search history.

(56) References Cited

U.S. PATENT DOCUMENTS

| | | | |
|---|---|---|---|
| 7,413,123 B2 * | 8/2008 | Ortenzi | A61M 5/14546 235/385 |
| 8,035,517 B2 | 10/2011 | Gibson | |
| 8,123,724 B2 | 2/2012 | Gillespie, III | |
| 8,446,280 B2 | 5/2013 | Ortenzi et al. | |
| 8,551,038 B2 * | 10/2013 | Tsoukalis | G06F 19/3468 604/66 |
| 9,452,267 B2 | 9/2016 | Reynolds et al. | |
| 9,789,245 B2 | 10/2017 | Tieck et al. | |
| 10,434,246 B2 * | 10/2019 | Silkaitis | G06F 19/3468 |
| 2003/0216692 A1 | 11/2003 | Fago et al. | |
| 2004/0051368 A1 | 3/2004 | Caputo et al. | |
| 2004/0225252 A1 * | 11/2004 | Gillespie, Jr. | G06F 19/3468 604/19 |
| 2009/0112333 A1 * | 4/2009 | Sahai | A61M 5/142 700/3 |
| 2010/0160857 A1 | 6/2010 | Pongpairochana et al. | |
| 2011/0166512 A1 | 7/2011 | Both et al. | |
| 2011/0264033 A1 | 10/2011 | Jensen et al. | |
| 2011/0306929 A1 | 12/2011 | Levesque et al. | |
| 2013/0211330 A1 | 8/2013 | Pedersen et al. | |
| 2013/0225945 A1 | 8/2013 | Prince et al. | |
| 2014/0142507 A1 | 5/2014 | Armes | |
| 2015/0001285 A1 | 1/2015 | Halbert et al. | |
| 2015/0126926 A1 | 5/2015 | Giambattista et al. | |
| 2015/0246176 A1 | 9/2015 | Navarro et al. | |
| 2015/0310185 A1 | 10/2015 | Shah | |
| 2016/0015885 A1 * | 1/2016 | Pananen | A61J 1/1481 604/111 |
| 2016/0051750 A1 * | 2/2016 | Tsoukalis | G06F 19/3468 604/151 |
| 2016/0082182 A1 | 3/2016 | Gregory et al. | |
| 2016/0175515 A1 | 6/2016 | McCullough | |
| 2017/0143902 A1 | 5/2017 | Hansen et al. | |
| 2017/0290974 A1 * | 10/2017 | Tsoukalis | A61M 39/22 |

FOREIGN PATENT DOCUMENTS

| | | |
|---|---|---|
| EP | 3106190 A1 | 12/2016 |
| FR | 2217026 A1 | 9/1974 |
| GB | 143084 A | 5/1920 |
| GB | 2145795 A | 4/1985 |
| WO | WO-2005072795 A2 | 8/2005 |
| WO | WO-2016033496 A1 | 3/2016 |

OTHER PUBLICATIONS

Center for Devices and Radiological Health. "Radio Frequency Wireless Technology in Medical Devices—Guidance." U.S. Food and Drug Administration, FDA, Aug. 14, 2013, (24 pages), https://www.fda.gov/regulatory-information/search-fda-guidance-documents/radio-frequency-wireless-technology-medical-devices-guidance-industry-and-fda-staff.
Fujitsu, "Application: Fujitsu RFID and Sensor Solution for Medical Device Traceability," https://www.fujitsu.com/us/Images/FUJITSU%20RFID%20for%20Medical%20Device%20Traceability.pdf, Aug. 2015, 2 pages.
International Search Report issued by the European Patent Office for International Patent Application No. PCT/EP2018/052802 dated May 14, 2018.
Written Opinion issued by the European Patent Office for International Patent Application No. PCT/EP2018/052802 dated May 14, 2018.
International Preliminary Report on Patentability issued by the European Patent Office for International Patent Application No. PCT/EP2018/052802 dated Sep. 17, 2019.
Office Action issued by the Russian Patent Office for Russian Patent Application No. 2019127657/14(054275), dated Jun. 1, 2021.
Search Report issued by the Russian Patent Office for Russian Patent Application No. 2019127657/14(054275), dated Jun. 1, 2021.

* cited by examiner

MEDICAL DEVICE, PROGRAMMING DEVICE, WIRELESS TERMINAL, AND MEDICAL SYSTEM

CROSS REFERENCE TO RELATED APPLICATIONS

This application is a national stage entry, filed under 35 U.S.C. 371, of International Application No. PCT/EP2018/052802, filed on Mar. 15, 2018, which claims the benefit of and priority to U.S. Provisional Application No. 62/471,377, filed Mar. 15, 2017, and claims the benefit of and priority to European Patent Application No. 17164156.6, filed Mar. 31, 2017, the entire contents of which are hereby incorporated herein by reference in their entireties and for all purposes.

The invention relates to a medical device, a programming device for a medical device, a wireless terminal for a medical device, and a medical system comprising a medical device and at least one of a programming device and a wireless terminal.

Medical devices, for example, injector devices, can be loaded with containers accommodating a pharmaceutical product. For a prescribed usage of the medical device, it is necessary to ensure that a correct container is loaded and used in the medical device. Furthermore, it is necessary to ensure that a correct pharmaceutical product is used with the medical device. For example, it has to be ensured that the medical device is not used with a pharmaceutical product that has expired.

EP 2 249 275 A1 relates to management of information relating to medical fluids, containers therefor, and medical fluid administration devices for administering such medical fluids to patients. Data tags (e.g., RFID tag) are associated with containers and can be electromagnetically read from and/or written to using an electromagnetic device that is associated with a medical fluid administration device.

The invention is directed at the object of providing an improved medical device which prevents erroneous usage of the medical device.

This object is addressed by a medical device as defined in claim 1, a programming device as defined in claim 11, a wireless terminal as defined in claim 13, and a medical system as defined in claim 15.

The medical device comprises a container receiver unit configured to receive and hold a container, wherein the container accommodates a pharmaceutical product and comprises a first communication tag configured to store information regarding the pharmaceutical product, a reader unit configured to wirelessly read the information from the first communication tag, and a control unit configured to control the medical device based on the information read from the first communication tag.

The medical device may be any kind of medical equipment that is adapted to be loaded with a container or cartridge that accommodates a pharmaceutical product. According to a preferred embodiment, the medical device is an injector device that is configured to eject a skin needle and dispense via the ejected skin needle a pharmaceutical product accommodated in a container through the skin of a human or animal body. In case the medical device is implemented as an injector device, the term "pharmaceutical product" is meant to encompass any medicament-containing flowable drug configured to be passed through a hollow needle of the injector device in a controlled manner, such as a liquid, solution, gel or fine suspension.

The container receiver unit may be any kind of mechanical holding unit that is adapted to receive and hold in a fixed manner the container. For example, the container receiver unit may be a container receptacle having a door or a shutter, or a container receptacle that can moved by means of a spring at least partly out of the medical device.

The first communication tag may be any kind of storage means that is adapted to store data that can be wirelessly read by the reader unit. In a preferred embodiment, the first communication tag is a near-field communication (NFC) tag and the reader unit is an NFC initiator device. The NFC tag may be any of the NFC types defined by the NFC Forum. The NFC tag may be read-only and can only be encoded by the manufacturer of the container. Alternatively, the NFC tag may also have reading and writing capabilities. In particular, the devices may operate in an NFC passive mode in which the initiator device provides a carrier field and the target device, i.e., the first communication tag, answers by modulating the carrier field. Since NFC systems are designed as short-range wireless technologies, typically requiring a maximum separation of 10 cm or less between the initiator device and the target device, NFC systems are preferably used in the medical devices of the present disclosure in order to prevent data manipulation via the air interface. Alternatively, the first communication tag may be a barcode or an ultra-high frequency (UHF) radio-frequency identification (RFID) tag.

The control unit may be any kind of control device, for example, a microcontroller, which is configured to control the medical device based on the information read from the first communication tag. For example, the control unit may prevent the medical device from dispensing the pharmaceutical product accommodated in the container in case the information read from the first communication tag indicates that the pharmaceutical product has expired.

According to a preferred embodiment, the medical device comprises an opening or a transparent window allowing to at least partially see from the outside the container inserted into the container receiver unit, wherein the reader unit comprises a first antenna unit, and the container inserted into the container receiver unit is located between (i) the opening or the transparent window and (ii) the first antenna unit.

The opening or transparent window may be provided at the housing of the medical device, preferably, in proximity to the location where the container can be inserted into the container receiver unit. The arrangement of the container between the opening or transparent window and the reader unit provides a double function of allowing a user of the medical device to view the container from the outside (for example, to read a printed label provided on the container), and ensuring that the reader unit can wirelessly read the information regarding the pharmaceutical product from the first communication tag. Thus, a double check of the container by the medical device and the user of the medical device is enabled.

According to a further preferred embodiment, in case the medical device comprises the opening allowing to at least partially see from the outside the container inserted into the container receiver unit and the container receiver unit holds the container, the container receiver unit is configured to allow a user of the medical device to rotate the container around its middle axis. For example, in case a label is provided on the container having a substantially cylindrical shape, however, the container is inserted such in the container receiver unit that the label cannot be seen from the outside, the user of the medical device can rotate with his fingers through the opening the container around its middle axis until the label is visible from the outside. For allowing this rotation, the container may be held in such a manner in the container receiver unit that only the distal and proximal ends of the container are supported in the container receiver unit.

For enabling to see the container from the outside through an opening or a transparent window and at the same time ensuring that the information from the first communication tag can be read via the first antenna unit, the first antenna unit may only partially surround the container inserted into the container receiver unit. Preferably, the first antenna unit and the opening or transparent window completely surround the container, i.e., the side area of a substantially cylindrically shaped container. Moreover, in a preferred embodiment, a cross section area of the first antenna unit surrounds between 50% and 30% of a cross section area of the container. Thus, component material and weight can be saved, which is of advantage if a handheld medical device is concerned.

In order to ensure that the information from the first communication tag can be read via the first antenna unit, the first antenna unit may comprise a first antenna part extending along a first plane and a second antenna part extending along a second plane. The first antenna part and the second antenna part may be separate antennas. Each of the first antenna part and the second antenna part may have a substantially square, circled, looped, or rectangular shape. For example, each of the first antenna part and the second antenna part may be at least one of a wire loop antenna and a stamp antenna. Each of the first antenna part and the second antenna part may also be any of the antenna classes defined in ISO/IEC 14443, which is herein incorporated by reference. Alternatively, the first antenna part and the second antenna part may also be parts of one flexible antenna.

Preferably, the first plane and the second plane cross each other with an angle in the range from 90° to 120°, wherein the angle faces the container inserted into the container receiver unit. With such an arrangement and orientation of the antenna parts, it is possible to ensure that at least one of the first antenna part and the second antenna part can detect signals from the first communication tag on the cartridge, even in case the container is rotated by the user.

According to another embodiment, the medical device comprises a second communication tag. The second communication tag may be configured to wirelessly receive and store information regarding at least one of prescription of the pharmaceutical product, setup of the medical device, debugging of the medical device, and calibration of the medical device. For example, the second communication tag is readable by the reader unit and/or an external device, and writeable by an external device. Similar to the first communication tag, the second communication tag may be an NFC tag. The second communication tag may be operated in a passive mode or an active mode. To maintain the sterility of a packaged medical device, the second communication tag allows programming the medical device from the outside without having to open the medical device. For example, by sending data to the second communication tag, it is possible to externally set run-time parameters of the medical device, e.g., an ejection speed for ejecting a skin needle from an injector device.

According to a preferred embodiment, the reader unit comprises a second antenna unit configured to read the information stored in the second communication tag, and the control unit is configured to control the medical device based on the information read from the second communication tag. For example, by means of a programming device that is configured to wirelessly write data in the second communication tag, a pharmacist may set certain parameters of the medical device at the point of sale, based on the prescription of the specific patient, but without requiring him/her to open the medical device and lose its sterility. The second communication tag may also be used for contactless transfer of information to the medical device for debug and setup purposes. For example, the information stored in the second communication tag may be used to enter the medical device into specific debug modes, such as a mode for calibrating sensors (e.g., a skin sensor) in the medical device, a mode for checking the angular detection ability of the first communication tag by the reader unit, and a system setup mode to modify parameters such as needle injection speed and/or skin sensor detection threshold of an injector device.

According to a preferred embodiment, the control unit may be configured to control the medical device based on the information read from the second communication tag and the information read from the first communication tag.

According to a another embodiment, the medical device further comprises a switch unit connected to the reader unit, wherein the reader unit comprises three antennas, and the switch unit is configured to consecutively switch signals received from the three antennas to the control unit. Preferably, a first antenna and a second antenna are used for reading the information stored in the first communication tag. Further, preferably, a third antenna is used for reading the information stored in the third communication tag. Thus, by means of rotational switching between the first to third antennas, data can be subsequently read via each of the first to third antennas.

According to one embodiment, the medical device further comprises a communication unit configured to wirelessly communicate with a wireless terminal, wherein the communication unit is further configured to send, in real-time, information regarding the status of the medical device to the wireless terminal, send debugging data concerning the medical device to the wireless terminal, and/or send data regarding usage of the medical device to the wireless terminal. For example, the communication unit may be a Bluetooth transceiver unit that is configured to communicate with a corresponding Bluetooth transceiver unit in a wireless terminal, e.g., a smartphone running a specific software or app that is programmed to process the received data. Thus, the wireless terminal receiving the data from the medical device can enable an enhanced functionality of the medical device, such as healthcare monitoring, monitoring of usage of the medical device, monitoring of adherence of the patient, tracking of past medication, ordering of new medication via the Internet, history look-up, dosage information check, providing guidance to the user on use-steps, and/or trouble-shooting. Additionally, the medical device and the wireless terminal may enter into a training mode in which the wireless terminal can track in real time the status of the medical device and show the user next steps to be executed in the form of animations, videos, or written explanations. The medical device and the wireless terminal may also enter into a debug mode in which a control software running on a processor in the medical device can be debugged using the connection between the medical device and the wireless terminal, and a corresponding app running on the wireless terminal to view internal variables of the medical device.

The invention further concerns a programming device comprising a sending unit configured to send information regarding at least one of prescription of a pharmaceutical product, setup of a medical device, debugging of a medical device, and calibration of a medical device to the medical device. Preferably, the programming device sends the information wirelessly to the medical device. The programming device may be any kind of computing device that is adapted to receive, process, and send data. In a preferred embodiment, the programming device comprises an NFC initiator device which is configured to wirelessly write data in the second communication tag, which is located in the medical device. The initiator device and the target device (i.e., the second communication tag) may operate in a passive mode. However, it is also possible that the initiator device and the target device operate in an active mode.

The programming device may further comprise a user interface, for example, a touch-sensitive screen displaying an app, which is configured to enter the information regarding at least one of prescription of a pharmaceutical product, setup of the medical device, debugging of the medical device, and calibration of the medical device. Moreover, in case the initiator device and the target device operate in an active mode, the programming device may further comprise a processing device that processes the data received from the second communication tag.

The invention further concerns a wireless terminal comprising a communication unit configured to wirelessly communicate with the medical device, wherein the communication unit is further configured to receive, in real-time, information regarding the status of the medical device from the medical device, receive debugging data concerning the medical device from the medical device, and/or receive data regarding usage of the medical device from the medical device. The wireless terminal may be any kind of wireless communication terminal, for example, a smartphone. The communication unit may, for example, comprise a Bluetooth transceiver unit that is configured to communicate with a corresponding Bluetooth transceiver unit in the medical device. Other wireless communication standards like Wi-Fi, LTE, WLAN, WiMAX or ZigBee may also be used for the communication between the medical device and the wireless terminal. Moreover, the wireless terminal may be configured to communicate via the Internet with an external web server that stores data related to the medical device and/or the user of the medical device.

According to one embodiment, the wireless terminal further comprises a processing unit configured to process the data received from the medical device. For example, the processing unit may receive, in real-time, information regarding the status of the medical device from the medical device, and may control a display unit in the wireless terminal to display animations, videos, and/or written explanations regarding next steps necessary to be executed by the user of the medical device.

The invention further concerns a medical system comprising a medical device, and at least one of a programming device and a wireless terminal.

Preferred embodiments of the invention will now be described in further detail with reference to the appended drawings, wherein:

FIG. 1 schematically shows a first medical device according to a first embodiment;

Figure 5:
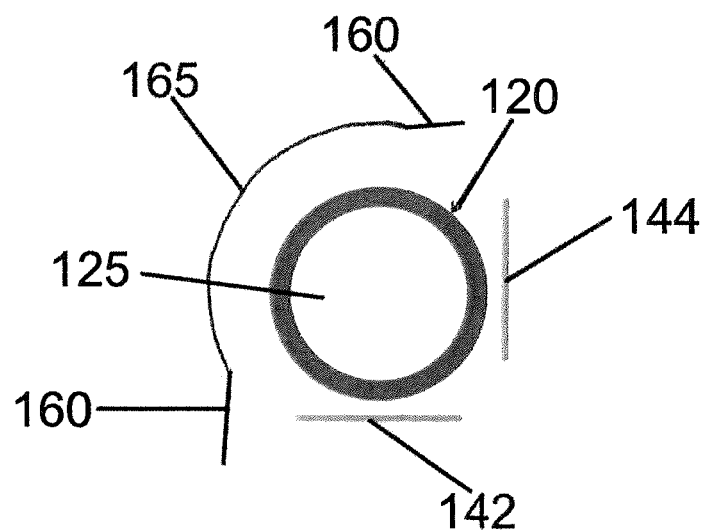
Figure 6:
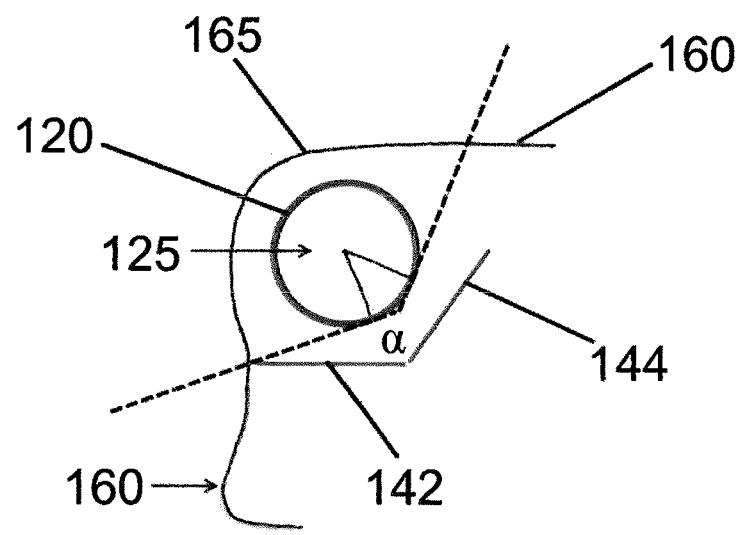
Figure 7:
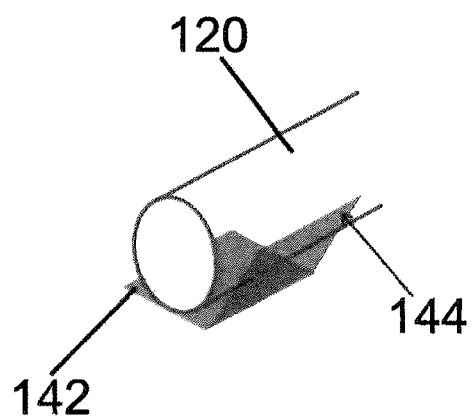
Figure 8:
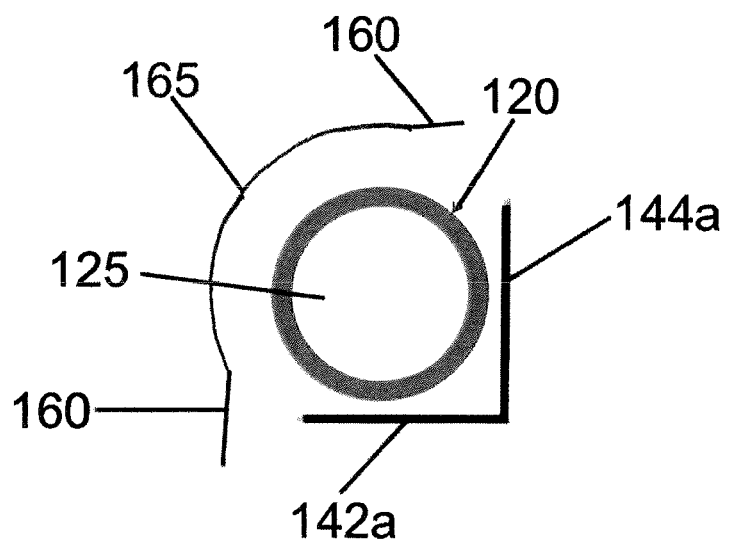
Figure 9:
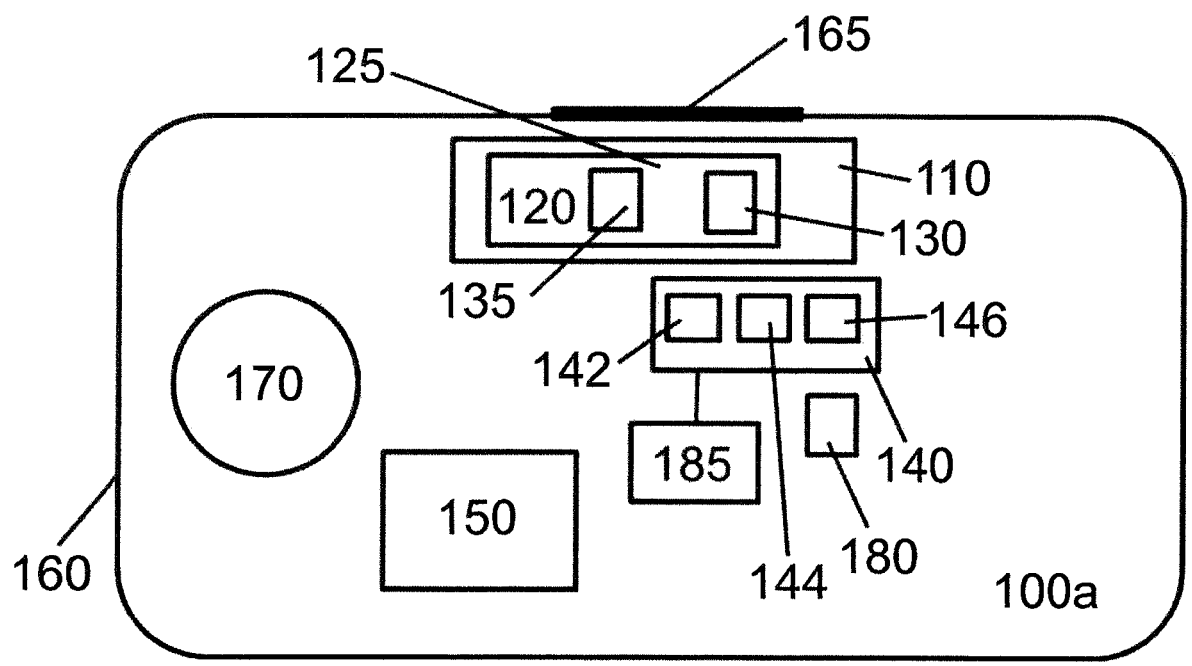
Figure 9:
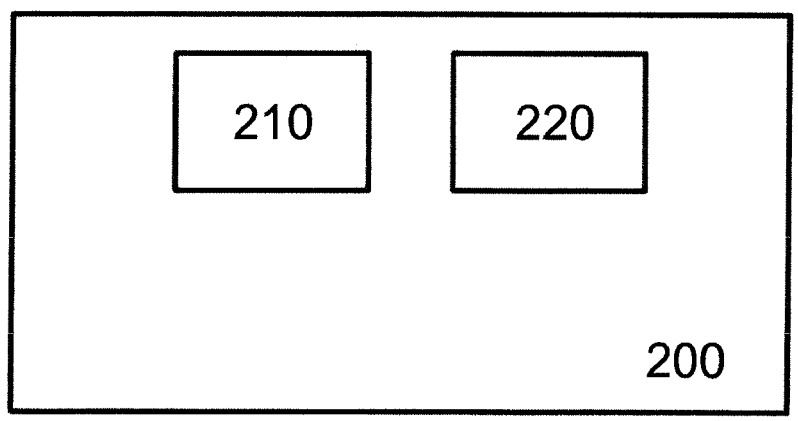
Figure 10:
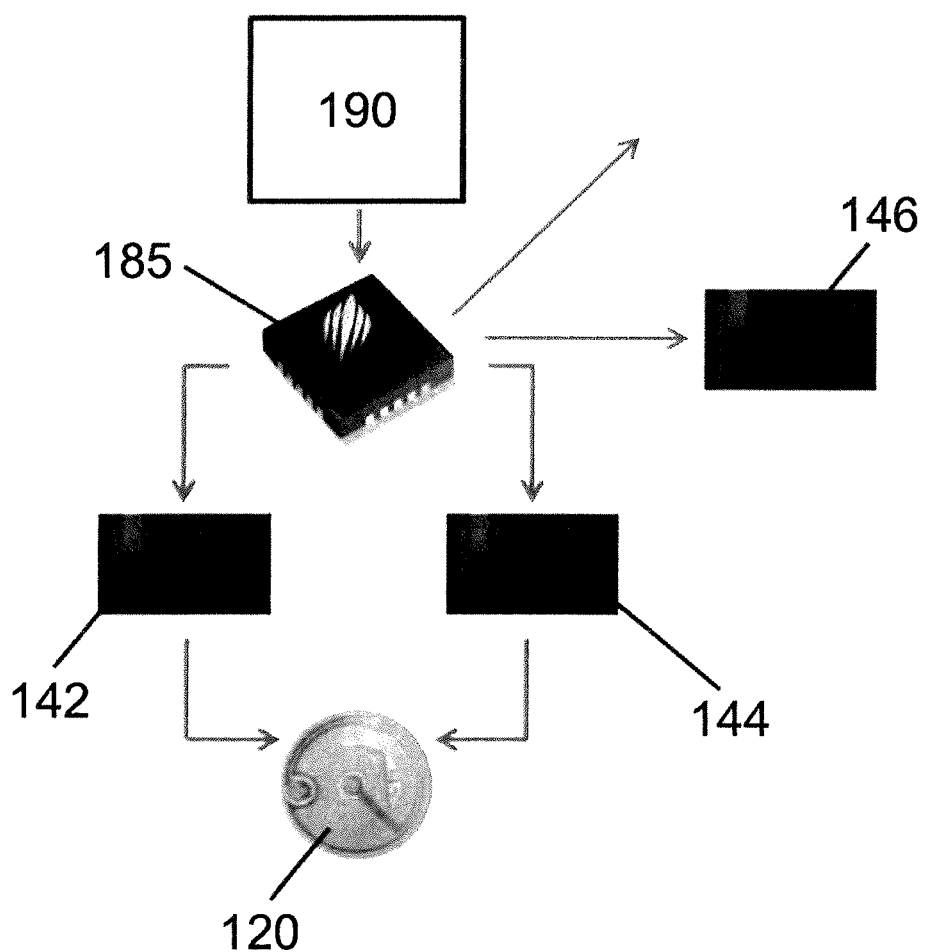

FIG. 5 schematically shows a partial cross section of a second medical device;

FIG. 6 schematically shows a partial cross section of a third medical device;

FIG. 7 schematically shows a partial perspective view of a fourth medical device;

FIG. 8 schematically shows a partial perspective view of a fourth medical device;

FIG. 9 schematically shows a medical system comprising a medical device and a programming device according to a second embodiment;

FIG. 10 schematically shows a receiving unit with a switching unit; and

Figure 11:
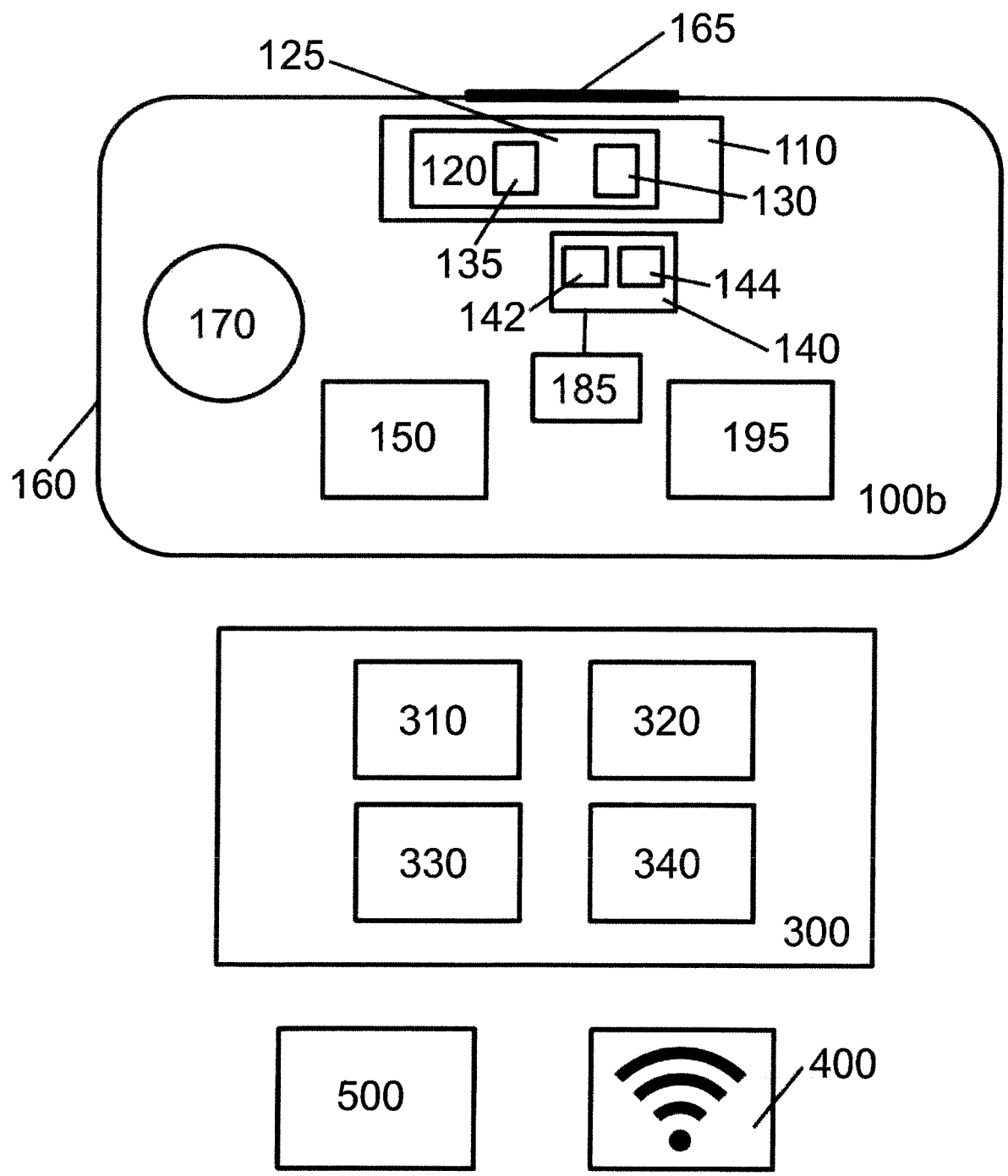

FIG. 11 schematically shows a medical system comprising a medical device and a wireless terminal according to a third embodiment.

Figure 1:
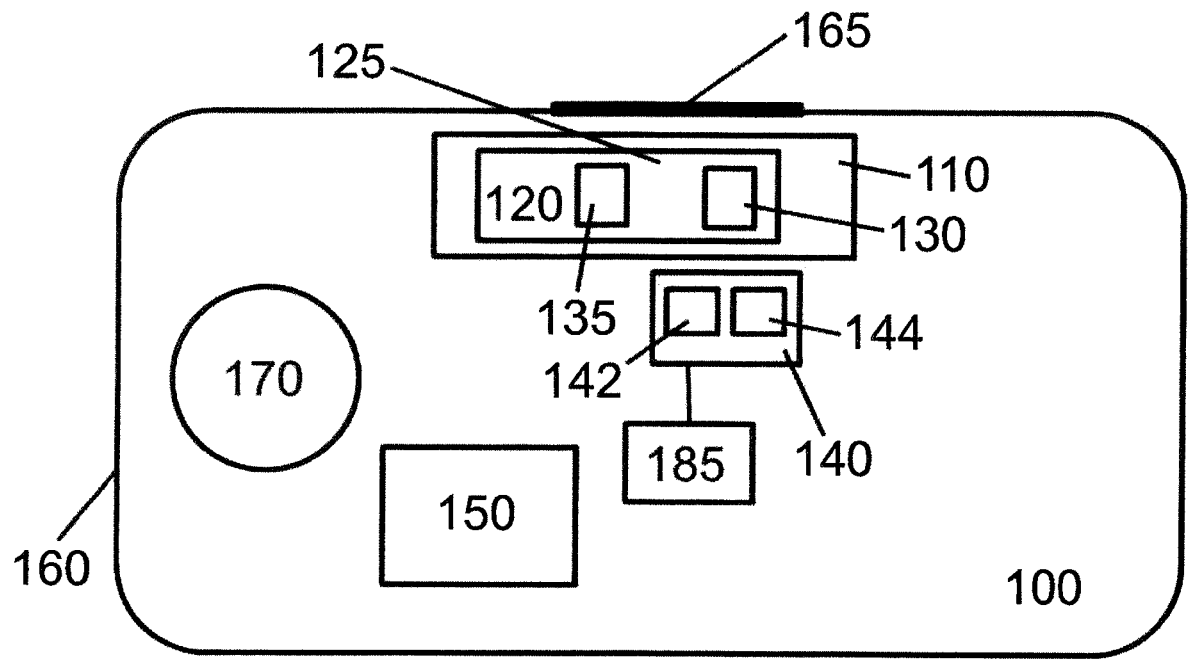

FIG. 1 schematically shows a first medical device 100 according to a first embodiment. The medical device 100 comprises a container receiver unit 110 configured to receive and hold a container 120, a reader unit 140 comprising a first antenna 142 and a second antenna 144, a control unit 150, an ignition button 170, and a switch unit 185 connected to the reader unit 140.

The components of the medical device 100 are provided in a housing 160. At one side of the housing 160, the medical device 100 comprises an opening 165. Instead of the opening 165, a transparent window may be provided. The opening 165 is provided at a location that is proximal to the container receiver unit 110 so that a container 120 inserted in the container receiver unit 110 can be seen from the is outside by a user when looking through the opening 165 into the medical device 100.

The container 120 is adapted to accommodate a pharmaceutical product 125 and comprises a label 135 which is fixed around the outer circumference of the container 120 and which presents information about the pharmaceutical product 125 accommodated in the container 120 (e.g., product name, batch number, expiry date, etc.). Furthermore, the container 120 comprises a first NFC tag 130 which is fixed around the outer circumference of the container 120 and which is configured to store information regarding the pharmaceutical product 125 (e.g., product name, batch number, expiry date, etc.). Thus, the opening or transparent window 165 may have any shape and size that allows a user to see the label 135, however, does not allow the container 120 to fall out of the medical device 100.

Figure 2:
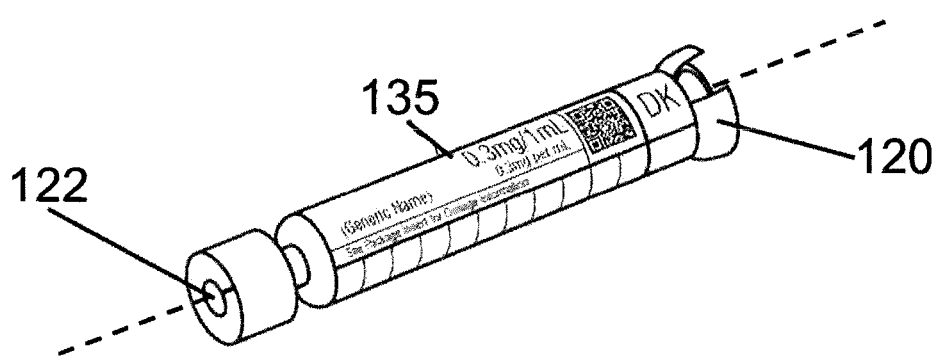
FIG. 2 shows an exemplary container.

FIG. 2 shows an example of a container 120 with a printed label 135 which is fixed around the outer circumference of the container 120. The container 120 has a substantially cylindrical shape. The dashed line in FIG. 2 indicates the middle axis of the container 120. At its distal end, the container 120 comprises a sealed dispensing port 122 through which a medical drug stored in the container 120 may be dispensed in case a piston provided in an axially movable manner in the container 120 pushes the medical drug (not shown in FIG. 2) through the dispensing port 122.

Figure 3:
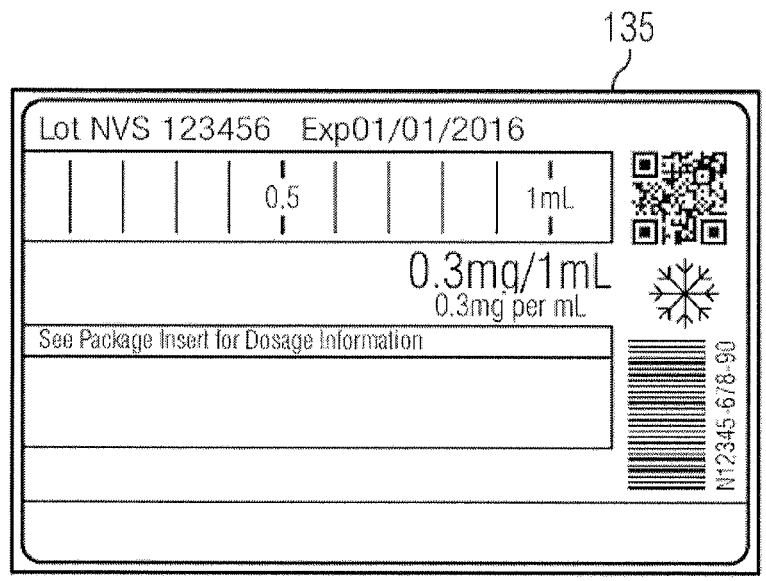
FIG. 3 shows an exemplary label for a container.

For illustrative purposes, FIG. 3 shows an exemplary label 135 in an un-affixed and an unwound form. The label 135 comprises an NFC tag 130 which is integrated in the sheet of the label 135 so that it is not visible from the outside (not shown in FIG. 3).

Figure 4:
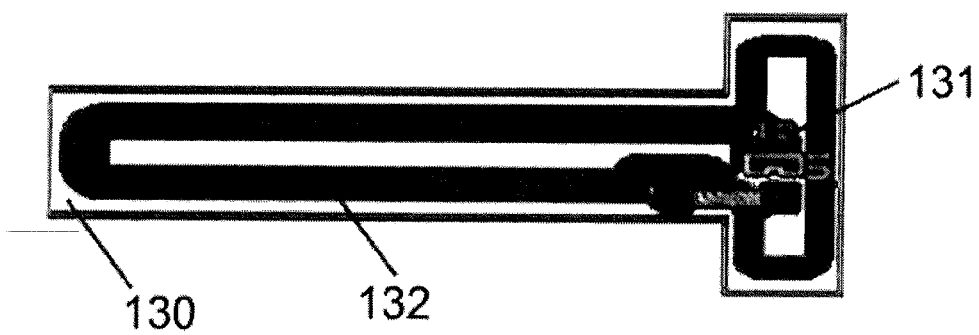
FIG. 4 shows an exemplary NFC tag.

For illustrative purposes, an exemplary NFC tag 130 is shown in FIG. 4 in a form detached from the label 135. The NFC tag 130 comprises a memory 131 in which information regarding the pharmaceutical product 125 is stored, and an RFID antenna 132. In the embodiment according to FIG. 4, the NFC tag 130 is designed to fit around the outer surface of a 3 ml container 120. Moreover, the NFC tag 130 is designed to be able to be read from all 360° angles when affixed to the container 120.

Now turning back to FIG. 1, the opening 165 provided in the housing 160 has such a size, and the container 120 inserted in the container receiver unit 110 is located in such proximity to the opening 165 that a user can touch with his fingers through the opening 165 the container 120. Thus, in case the user cannot appropriately read the label 135, he/she may rotate the container 120 with his/her fingers within the container receiver unit 110. For this, the container receiver unit 110 may be structured such that it only supports the container 120 at is distal end and its proximal end so that it may be rotated within the container receiver unit 110 around its middle axis (see FIG. 2). Specifically, even during the time when the container 120 is rotated by the user, the first antenna 142 and the second antenna 144 enable reading of the information stored in the first NFC tag 130.

Moreover, the opening 165 may be included in a door or a shutter, or any other access mechanism that may be used for inserting the container 120 into the medical device 100, i.e., into the container receiver unit 110.

The reader unit 140 is configured to wirelessly read the information from the first NFC tag 130, and the control unit 150 is configured to control the medical device 100 based on the information read from the first NFC tag 130. For example, when the first NFC tag 130 stores data regarding the expiry date of the pharmaceutical product 125, and the reader unit 140 reads this information from the first NFC tag 130, the control unit 150 may process the received information and control the medical device 100 such that a dispensing of the pharmaceutical product 125, which has expired, is not possible. For this, the control unit 150 may control the medical device 100 such that when a user presses the ignition button 170, the medical device 100 does not dispense the pharmaceutical product 125 from the medical device 100.

To allow a user to read the label 135 from the outside and at the same ensure that the reader unit 140 can read the data from the first NFC tag 140, the container receiver unit 110 is provided between the opening 165 and the reader unit 130. In particular, the opening 165 and the reader unit 140 are provided directly at the container receiver unit 110 holding the container 120.

The switch unit 185 is adapted to switch the input signals received via each of the first antenna 142 and the second antenna 144 in a rotational manner to the control unit 150. For this, the switch unit 185 is controlled by the control unit 150. Accordingly, the data stored in the first NFC tag 130 can be read via the first antenna 142 and the second antenna 144.

FIG. 5 schematically shows a partial cross section of a second medical device. The second medical device corresponds to the first medical device 100 shown in FIG. 1 so that the same reference numbers concern the same elements.

Contrary to the first medical device 100 shown in FIG. 1, the second medical device partly shown in FIG. 5 comprises at the housing 160 a transparent window 165 instead of the opening. However, similar technical effects may also be achieved with an opening.

Specifically, FIG. 5 shows as an exemplary embodiment illustrating how the first antenna 142 and the second antenna 144 may be arranged with regard to the container 120 so that the first NFC tag 130 (not shown in FIG. 5) can always be read via at least one the first antenna 142 and the second antenna 144, and the label 135 (not shown in FIG. 6) can be seen from the outside through the transparent window 165.

The first antenna 142 extends along a first plane, and the second antenna 144 extends along a second plane. Each of the first antenna 142 and the second antenna 144 has a substantially square shape. In its cross section shown in FIG. 5, the first antenna 142 has a length that is smaller than the diameter of the container 120. Moreover, in its cross section shown in FIG. 5, the second antenna 144 has a length that is smaller than the diameter of the container 120. The first plane and the second plane are substantially perpendicular to each other. Thus, the first antenna 142 together with the second antenna 144 only partially surround the container 120. In particular, a cross section area of the first antenna 142 together with the second antenna 144 surrounds between 50% and 30% of a cross section area of the container 120. Thus, it can be ensured that in whatever rotational direction the container 120 is inserted in the container receiving unit 110 (not shown in FIG. 5), either the first antenna 142 or the second antenna 144 can read the data stored in first NFC tag 130, and the user can read the label 135 from the outside through the transparent window 165. Thus, at any given angle, at least one of the first antenna 142 or the second antenna 144 has sufficient overlap with the container 120.

FIG. 6 schematically shows a partial cross section of a third medical device. The third medical device corresponds to the first medical device 100 shown in FIG. 1 so that the same reference numbers concern the same elements.

Contrary to the first medical device 100 shown in FIG. 1, the third medical device partly shown in FIG. 6 comprises a transparent window 165 instead of the opening. However, similar technical effects may also be achieved with an opening. Moreover, contrary to the second medical device shown in FIG. 5, in the third medical device shown in FIG. 6, the transparent window 165 has a larger size. Specifically, as is indicated by the dashed lines in FIG. 6, a larger area of sight through the transparent window 165, which is provided in the housing 160, is foreseen.

Similar to the embodiment according to FIG. 5, in the embodiment according to FIG. 6, the first antenna 142 extends along a first plane, and the second antenna 144 extends along a second plane. Moreover, each of the first antenna 142 and the second antenna 144 has a substantially square shape. However, contrary to the embodiment according to FIG. 5, in the embodiment according to FIG. 6, the first axis and the second axis cross each other with an angle α, which is larger than 90°. Preferably, the angle α is in the range from 90° to 120°. Thus, in its cross section, the first antenna 142 and the second antenna 144 are V-shaped. Further preferably, in the cross sectional view shown in FIG. 6, each of the first antenna 142 and the second antenna 144 has a length that approximately corresponds to the diameter of the container 120.

FIG. 7 schematically shows a partial perspective view of a fourth medical device. The fourth medical device corresponds to the first medical device 100 shown in FIG. 1 and the third medical device shown in FIG. 6 so that the same reference numbers concern the same elements. From the partial perspective view shown in FIG. 7, the plane areas of the first antenna 142 and the second antenna 144 can be seen. Although each of the first antenna 142 and the second antenna 144 shown in FIG. 7 has a substantially rectangular shape, each of the first antenna 142 and the second antenna 144 may also have another shape, e.g., a substantially square, circled, or looped shape.

FIG. 8 schematically shows a partial perspective view of a fourth medical device. The medical device shown in FIG. 8 may be the medical device 100 shown in FIG. 1. The medical device shown in FIG. 8 is similar to the medical device shown in FIG. 5, however, differs from the medical device shown in FIG. 5 in that only one flexible antenna having a first antenna part 142a and a second antenna part 144a is provided. The flexible antenna may consist of a flexible substrate onto which an antenna circuit is printed.

The medical device shown in FIG. 8 has a substantially rectangular shape and is bent with an angle of 90°. However, other shapes and other bending angles are possible, e.g., the shapes and angles described with regard to FIGS. 1 and 5 to 7.

FIG. 9 schematically shows a medical system comprising a medical device 100a and a programming device 200 according to a second embodiment. The medical device 100a shown in FIG. 9 is based on the medical device 100 shown in FIG. 1 so that the same reference numbers concern the same elements and any repeated explanation thereof is omitted.

In addition to the medical device 100 according to the first embodiment shown in FIG. 1, the medical device 100a according to the second embodiment shown in FIG. 9 comprises a second NFC tag 180, and the receiver unit 140 comprises a third antenna 146.

The second NFC tag 180 is provided in a fixed manner in the medical device 100a. Preferably, the second NFC tag 180 is provided at a location in proximity to the third antenna 146 so that the data stored in the second NFC tag 130 can be read via the third antenna 146. Based on the information read via the third antenna 146 from the second NFC tag 180, the control unit 150 can control the medical device 100a. For example, the control unit 150 can obtain and process the information from both the first NFC tag 130 and the second NFC tag 180 before allowing the medical device 100a to dispense the pharmaceutical product 125 from the container 120.

The second NFC tag 180 is configured to wirelessly receive and store information regarding at least one of prescription of the pharmaceutical product 125, setup of the medical device 100a, debugging of the medical device 100a, and calibration of the medical device 100a. Thus, based on any of this information, the control unit 150 may control the medical device 100a, i.e., components of the medical device 100a.

The switch unit 185 is adapted to switch the input signals received via each of the first antenna 142, the second antenna 144, and the third antenna 146 in a rotational manner to the control unit 150. For this, the switch unit 185 is controlled by the control unit 150. Accordingly, the data stored in the first NFC tag 130 can be read via the first antenna 142 and the second antenna 144, and the data stored in the second NFC tag 180 can be read via the third antenna 146.

The medical system 100a shown in FIG. 9 further comprises a programming device 200. The programming device 200 comprises a sending unit 210 and a user interface 220.

The sending unit 210 is configured to send information regarding at least one of prescription of pharmaceutical product 125, setup of the medical device 100a, debugging of the medical device 100a, and calibration of the medical device 100a to the medical device 100a. Specifically, the sending unit 210 is configured to send any of this information to the second NFC tag 180, which stores the received information in its memory. The sending unit 220 may, for example, be an NFC initiator device. The sending unit 220 and the second NFC tag 180 may operate in a passive mode. However, the sending unit 220 and the second NFC tag 180 may also operate in an active mode. In this case, the programming device 200 additionally comprises a processing unit (not shown in FIG. 9) configured to process the data received from the second NFC tag 180.

The user interface 220 is configured to enter the information regarding at least one of prescription of a pharmaceutical product 125, setup of the medical device 100a, debugging of the medical device 100a and calibration of the medical device 100a into the programming device 200. Accordingly, a pharmacist may use the programming device 200 to set certain parameters of the medical device 100a at the point of sale without requiring him/her to open the medical device 100a and lose its sterility. Moreover, the programming device 200 may be used for transferring information to the second NFC tag 180, which may be used by the control unit 150 to enter the medical device 100 into specific debug modes, such as a mode for calibrating sensors in the medical device 100a (e.g., a skin sensor in an injector device), a mode for checking the angular detection ability of the first NFC tag 130 by the reader unit 140, and a system setup mode to modify parameters such as needle injection speed and/or skin sensor detection threshold when the medical device 100a is implemented as an injector device.

Data received from the second NFC tag 180 operating in an active mode and processed by the processing unit may also be displayed in a display of the user interface 220.

FIG. 10 schematically shows an example of a receiving unit 142, 144, 146 with a switch unit 185. The receiving unit 142, 144, 146 and the switch unit 185 may be the units shown in FIG. 9. Thus, the same reference numbers concern the same elements.

As can be seen from FIG. 10, an RFID reader/writer integrated circuit 190 is connected to the switch unit 185. The switch unit 185 is adapted to split four input signals into four channels, as indicated by the four arrows originating from switch unit 185. Thus, in this exemplary embodiment, up to four antennas can be connected to the switch unit 185. However, only the first antenna 142, the second antenna 144, and the third antenna 146 are connected to the switch unit 185, whereas the fourth input is not used. Thus, the switch unit 185 can read each of the first antenna 142, the second antenna 144, and the third antenna 146 in a rotational manner. Accordingly, it can be ensured that at least one of the first antenna 142 and the second antenna 144 detects the first NFC tag 130 (not shown in FIG. 10) provided on the container 120.

FIG. 11 schematically shows a medical system comprising a medical device 100b and a wireless terminal 300 according to a third embodiment.

The medical device 100b according to the third embodiment shown in FIG. 11 is based on the medical device 100 according to the first embodiment shown in FIG. 1.

Thus, the same reference numbers concern the same components and any repeated explanation thereof is omitted.

Moreover, the third embodiment according to FIG. 11 may be combined with the second embodiment according to FIG. 9, i.e., the elements additionally shown in the medical device 100a of FIG. 9 may be included in the medical device 100b shown in FIG. 11. Moreover, the programming device 200 shown in FIG. 9 may additionally be provided in the medical system of the third embodiment according to FIG. 11.

The medical device 100b according to the third embodiment shown in FIG. 11 differs from the medical device 100 according to the first embodiment shown in FIG. 1 in that a communication unit 195 is additionally provided in the medical device 100b. The communication unit 195 is a Bluetooth transceiver unit which is configured to wirelessly communicate with a wireless terminal 300.

The wireless terminal 300 comprises a first communication unit 310 implemented as a Bluetooth transceiver unit which is configured to wirelessly communicate with the communication unit 195 in the medical device 100b. Furthermore, the wireless terminal 300 comprises a processing unit 320, a display unit 330, and a second communication unit 340.

The communication unit 195 of the medical device 100b is connected to the control unit 150. The control unit 150 controls the sending of data from the communication unit 195 via an air interface to the first communication unit 310. Specifically, the control unit 150 controls the communication unit 195 to send to the first communication unit 320 in the wireless terminal 300, in real-time, information regarding the status of the medical device 100b. The communication unit 195 may also or additionally send debugging data concerning the medical device 100b, and/or data regarding usage of the medical device 100b to the first communication unit 320.

The processing unit 320 in the wireless terminal 300 is configured to process the data received from the medical device 100b. For example, the processing unit 320 receives, in real-time, information regarding the status of the medical device 100b and controls the display unit 330 to display animations, videos, and/or written explanations regarding next steps necessary to be executed by the user of the medical device 100b.

The second communication unit 340 is configured to setup a connection to the Internet. For this, the second communication unit 340 is realized as a wireless local area network (WLAN) module. Alternatively, the second communication unit 340 may also be realized as a long-term evolution (LTE) module or any other wireless module that is configured to setup a connection to the Internet. Via a WLAN router 400, the WLAN module 340 is configured to setup a connection to the Internet and communicate with a web server 500.

The web server 500 may, for example, belong to a pharmaceutical company or a pharmacist so that a new container 120 can be ordered by the wireless terminal 300 in case the information received from the medical device 100b and/or the information stored in the wireless terminal 300 indicates that the user of the medical device 100b requires a new container 120. Moreover, the web server 500 may store data regarding update and/or debugging of the medical device 100b. The information received from the medical device 100b may be sent to the web server 500 in order to compare the information with data from other medical devices.

The invention claimed is:

1. A medical device, comprising:
a container receiver unit configured to receive and hold a container, the container accommodating a pharmaceutical product and comprising a first communication tag configured to store information regarding the pharmaceutical product;
a reader unit configured to wirelessly read the information from the first communication tag;
a control unit configured to control the medical device based on the information read from the first communication tag; and
a second communication tag provided in a fixed manner inside a housing of the medical device such that the second communication tag remains inside the medical device (i) when the container receiver unit receives and holds the container and (ii) when the container is removed from the container receiver unit, and configured to wirelessly receive and store information regarding at least one of prescription of the pharmaceutical product, setup of run-time parameters of the medical device, and debugging of the medical device,
wherein the reader unit is configured to wirelessly read the information stored in the second communication tag, and the control unit is configured to control the medical device based on the information read from the second communication tag.

2. The medical device according to claim 1, comprising an opening or a transparent window allowing at least partial visibility of the container inserted into the container receiver unit from the outside, wherein
the reader unit comprises a first antenna unit, and
the container inserted into the container receiver unit is located between (i) the opening or the transparent window and (ii) the first antenna unit.

3. The medical device according to claim 2, wherein when the medical device comprises the opening and the container receiver unit holds the container, the container receiver unit is configured to allow a user of the medical device to rotate the container around its middle axis.

4. The medical device according to claim 2, wherein the first antenna unit only partially surrounds the container inserted into the container receiver unit.

5. The medical device according to claim 2, wherein the first antenna unit comprises a first antenna part extending along a first plane and a second antenna part extending along a second plane, wherein the first plane and the second plane cross each other with an angle ($\alpha$) in the range from 90° to 120°, and the angle ($\alpha$) faces the container inserted into the container receiver unit.

6. The medical device according to claim 1, wherein the reader unit comprises a second antenna unit configured to read the information stored in the second communication tag.

7. The medical device according to claim 1, further comprising:
a switch unit connected to the reader unit,
wherein the reader unit comprises three antennas, and the switch unit is configured to consecutively switch signals received from the three antennas.

8. The medical device according to claim 1, further comprising:
a communication unit configured to wirelessly communicate with a wireless terminal, wherein the communication unit is further configured to send at least one selected from the group comprising:
send, in real-time, information regarding the status of the medical device to the wireless terminal,
send debugging data concerning the medical device to the wireless terminal, and
send data regarding usage of the medical device to the wireless terminal.

9. The medical device according to claim 1, wherein the medical device is an injector device.

10. A programming device, comprising:
a sending unit configured to send information regarding at least one of the prescription of the pharmaceutical product, the setup of the medical device, and the debugging of the medical device to the medical device of claim 1.

11. The programming device of claim 10, further comprising:
a user interface configured to enter the information regarding at least one of the prescription of the pharmaceutical product, the setup of the medical device, the debugging of the medical device.

12. A wireless terminal, comprising:
a communication unit configured to wirelessly communicate with the medical device of claim 1, wherein the communication unit is further configured to receive at least one selected from the group comprising:

receive, in real-time, information regarding the status of the medical device from the medical device, receive debugging data concerning the medical device from the medical device, and receive data regarding usage of the medical device from the medical device.

13. The wireless terminal of claim 12, further comprising a processing unit configured to process the data received from the medical device.

14. A medical system comprising:

the medical device of claim 1; and a programming device comprising a sending unit configured to send information regarding at least one of the prescription of the pharmaceutical product, the setup of the medical device, and the debugging of the medical device; and a wireless terminal comprising a communication unit configured to wirelessly communicate with the medical device, wherein the communication unit is further configured to receive at least one selected from the group comprising:

receive, in real-time, information regarding the status of the medical device from the medical device, receive debugging data concerning the medical device from the medical device, and receive data regarding usage of the medical device from the medical device.

* * * * *